(12) United States Patent
Dubois et al.

(10) Patent No.: US 7,655,818 B2
(45) Date of Patent: *Feb. 2, 2010

(54) PROCESS FOR DEHYDRATING GLYCEROL TO ACROLEIN

(75) Inventors: Jean-Luc Dubois, Millery (FR); Christophe Duquenne, Zickau (DE); Wolfgang Holderich, Frankenthal (DE); Jacques Kervennal, Lyons (FR)

(73) Assignee: Arkema France, Colombes (FR)

( * ) Notice: Subject to any disclaimer, the term of this patent is extended or adjusted under 35 U.S.C. 154(b) by 59 days.

This patent is subject to a terminal disclaimer.

(21) Appl. No.: 11/814,830

(22) PCT Filed: Jan. 6, 2006

(86) PCT No.: PCT/EP2006/000736

§ 371 (c)(1),
(2), (4) Date: Jul. 26, 2007

(87) PCT Pub. No.: WO2006/087084

PCT Pub. Date: Aug. 24, 2006

(65) Prior Publication Data

US 2008/0214880 A1   Sep. 4, 2008

Related U.S. Application Data

(60) Provisional application No. 60/689,318, filed on Jun. 10, 2005.

(30) Foreign Application Priority Data

Feb. 15, 2005   (FR) .................................. 05 01500

(51) Int. Cl.
   C07C 45/52   (2006.01)
(52) U.S. Cl. ....................... 568/485; 568/486
(58) Field of Classification Search ................. 568/485, 568/486
   See application file for complete search history.

(56) References Cited

U.S. PATENT DOCUMENTS

| 2,558,520 | A |   | 6/1951 | Hoyt et al. |
| 5,387,720 | A |   | 2/1995 | Neher et al. |
| 5,387,721 | A |   | 2/1995 | Kruse et al. |
| 6,080,898 | A |   | 6/2000 | Drent et al. |
| 7,396,962 | B1 | * | 7/2008 | Dubois et al. ............... 568/485 |
| 2004/0015012 | A1 |   | 1/2004 | Hammon et al. |
| 2005/0021851 | A1 |   | 1/2005 | Hamynen |
| 2007/0129570 | A1 |   | 6/2007 | Shima et al. |

FOREIGN PATENT DOCUMENTS

| CN | 1 394 839 | 2/2003 |
| EP | 1 147 807 | 10/2001 |
| EP | 995 491 | 7/2003 |
| FR | 695 931 | 5/1930 |
| FR | 796553 | 4/1936 |
| JP | 5-293375 | 11/1993 |
| JP | 9-100244 | 4/1997 |
| WO | WO 2004/094357 | 11/2004 |

OTHER PUBLICATIONS

Dao et al., Reactions of Model Compounds of Biomass-Pyrolysis Oils over ZSM-5 Zeolite Catalyst, American Chemical Society, 1988.
Hashimoto, K., A Relationship Between Hammett Acidity Functions and Activatino Energy of Desorption of Ammonia, 60th CATSI Meeting Abstracts: No. 1F04, vol. 29, No. 6, 1987.
Tanabe, K., "Catalysis by Novel Sold Strong Acids and Super Acids", Heterogeneous Catalysis, pp. 71-94. Apr. 1984.
Wilson, N., et al., "On-Chip Catalysis Using a Lithographically Fabricated Glass Microreactor—The Dehydration of Alcohols Using Sulfated Zirconia", Chem. Comm., 2000, 733-734.
Ishida, T. et al., "Acid Property of Sulfur-Promoted Zirconium Oxide on Silica as Solid Superacid", Chemistry Letters, pp. 1869-1872, 1988.

* cited by examiner

*Primary Examiner*—Sikarl A Witherspoon
(74) *Attorney, Agent, or Firm*—Steven D. Boyd

(57) ABSTRACT

The present invention relates to a process for manufacturing acrolein by gas-phase dehydration of glycerol in the presence of strongly acidic solid catalysts with a Hammett acidity $H_0$ of between −9 and −18 and preferably between −10 and −16.

12 Claims, No Drawings

PROCESS FOR DEHYDRATING GLYCEROL TO ACROLEIN

The present invention relates to a process for manufacturing acrolein by gas-phase dehydration of glycerol.

Acrolein is the simplest of the unsaturated aldehydes. It is also known as 2-propenal, acrylaldehyde or acrylic aldehyde. As a result of its structure, acrolein has high reactive power by virtue of the presence of its two reactive functions, which are capable of reacting individually or together. It is for this reason that acrolein finds many applications, especially as a synthetic intermediate. It is in particular a key intermediate for the synthesis of methionine, a synthetic protein used as an animal feed supplement, which has established itself as a substitute for fishmeal. Acrolein is a non-isolated synthetic intermediate of acrylic acid in the industrial production of acrylic acid by catalytic oxidation of propylene in the gas phase. The importance of the chemistry of acrylic acid and its derivatives is known. Acrolein also leads, via reaction with methyl vinyl ether followed by hydrolysis, to glutaraldehyde, which has many uses in leather tanning, as a biocidal agent in oil well drilling and during the processing of cutting oils, and as a chemical disinfectant and sterilizing agent for hospital equipment.

Acrolein is usually used as a synthetic intermediate of derivatives that are synthesized on the site of production to minimize the transportation of acrolein from the manufacturer to the client. The essential reason is linked to the toxicity of acrolein, which leads industrials to avoid the storage and transportation of this chemical product.

The most commonly used process for producing acrolein is based on the gas-phase catalytic oxidation reaction of propylene with atmospheric oxygen. The acrolein thus obtained may then be incorporated directly into an acrylic acid manufacturing process. When acrolein is used as starting material for the synthesis of methionine or for fine chemistry reactions, a purification section allows the removal of the reaction by-products, mainly carbon oxides, acrylic acid, acetic acid and acetaldehyde.

The production of acrolein is thus highly dependent on the propylene starting material obtained by steam cracking or catalytic cracking of petroleum fractions. This starting material, of fossil origin, furthermore contributes towards increasing the greenhouse effect. It thus appears necessary to have available an acrolein synthesis process that is not dependent on propylene as resource and that uses another starting material, which is preferably renewable. This process would be particularly advantageous for the synthesis of methionine, which might then be said to be "obtained from biomass". Specifically, during its use in animal feed, methionine is rapidly metabolized and the carbon dioxide expelled into the atmosphere contributes towards increasing the greenhouse effect. If acrolein is obtained from a renewable starting material, for example obtained from plant oil, the $CO_2$ emissions no longer enter into the process balance, since they compensate for the carbon dioxide used by the biomass for its growth; there is therefore no increase in the greenhouse effect. Such a process thus satisfies the criteria associated with the new concept of "green chemistry" within a more global context of durable development.

It has been known for a long time that glycerol can lead to the production of acrolein. Glycerol (also known as glycerine) is derived from the methanolysis of plant oils at the same time as the methyl esters, which are themselves used especially as fuels or combustibles in diesel and domestic fuel oil. It is a natural product that has an "environmentally friendly" image, is available in large amount and may be stored and transported without difficulty. Many studies have been devoted to the financial upgrading of glycerol according to its degree of purity, and the dehydration of glycerol to acrolein is one of the routes envisaged.

The reaction involved for obtaining acrolein from glycerol is:

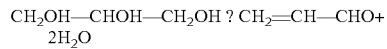

As a general rule, the hydration reaction is favoured at low temperatures, and the dehydration reaction is favoured at high temperatures. To obtain acrolein, it is thus necessary to use a sufficient temperature, and/or partial vacuum to shift the reaction. The reaction may be performed in the liquid phase or in the gas phase. This type of reaction is known to be catalysed by acids.

According to patent FR 695 931, acrolein is obtained by passing glycerol vapours at a sufficiently high temperature over salts of acids containing at least three acid functions, for instance phosphoric acid salts. The yields indicated are greater than 75% after fractional distillation.

In U.S. Pat. No. 2,558,520, the dehydration reaction is performed in the gas/liquid phase in the presence of diatomaceous earths impregnated with phosphoric acid salts, suspended in an aromatic solvent. A degree of conversion of the glycerol into acrolein of 72.3% is obtained under these conditions.

The process described in patent application WO 99/05085 is based on a complex homogeneous catalysis, under a $CO/H_2$ atmosphere at a pressure of 20/40 bar and in the presence of a solvent such as an aqueous solution of sulfolane.

Chinese patent application CN 1 394 839 relates to a process for preparing 3-hydroxypropanaldehyde from glycerol. The acrolein produced as reaction intermediate is obtained by passing vaporized pure glycerol over a catalyst of potassium sulfate or magnesium sulfate type. The reaction yields are not given.

U.S. Pat. No. 5,387,720 describes a process for producing acrolein by dehydration of glycerol, in the liquid phase or in the gas phase over acidic solid catalysts defined by their Hammett acidity. The catalysts must have a Hammett acidity of less than +2 and preferably less than −3. These catalysts correspond, for example, to natural or synthetic siliceous materials, for instance mordenite, montmorillonite, acidic zeolites; supports, such as oxides or siliceous materials, for example alumina ($Al_2O_3$), titanium oxide ($TiO_2$), coated with mono-, di- or triacidic inorganic acids; oxides or mixed oxides such as gamma-alumina, the mixed oxide ZnO—$Al_2O_3$, or alternatively heteropolyacids. According to the said patent, an aqueous solution comprising from 10% to 40% of glycerol is used, and the process is performed at temperatures of between 180° C. and 340° C. in the liquid phase, and between 250° C. and 340° C. in the gas phase. According to the authors of the said patent, the gas-phase reaction is preferable since it enables a degree of conversion of the glycerol of close to 100% to be obtained, which leads to an aqueous acrolein solution containing side products. A proportion of about 10% of the glycerol is converted into hydroxypropanone, which is present as the major by-product in the acrolein solution. The acrolein is recovered and purified by fractional condensation or distillation. For a liquid-phase reaction, a conversion limited to 15-25% is desired, to avoid excessive loss of selectivity. In the case of a gas-phase reaction, catalysts with an acidity $H_0$ of between +2 and −8.2 and preferably between −3 and −5.6 are the ones most advantageously used, whereas the liquid-phase reaction is preferably performed with catalysts with an acidity $H_0$ of between −8.2 and −20. U.S. Pat. No. 5,426,249 describes the same gas-phase process for the dehydration of glycerol to acrolein, but followed by a hydration of the acrolein and a hydrogenation to lead to 1,2- and 1,3-propanediol.

The dehydration reaction of glycerol to acrolein is thus generally accompanied by side reactions leading to the formation of by-products such as hydroxypropanone, propanaldehyde, acetaldehyde, acetone, adducts of acrolein with glycerol, glycerol polycondensation products, cyclic glycerol ethers, etc., but also phenol and polyaromatic compounds, which are the cause of the formation of coke on the catalyst. This results, firstly, in a reduction in the yield of and the selectivity towards acrolein, and secondly in deactivation of the catalyst. The presence of by-products in the acrolein, such as hydroxypropanone or propanaldehyde, some of which are moreover difficult to isolate, necessitates separation and purification steps, which lead to high recovery costs for the purified acrolein. Moreover, it is necessary to regenerate the catalyst very regularly in order to regain satisfactory catalytic activity.

The Applicant Company has found, surprisingly, that certain acidic solids with a Hammett acidity $H_0$ of between −9 and −18 have higher catalytic activity for the gas-phase dehydration reaction of glycerol to acrolein than the solids of lower acidity described in U.S. Pat. No. 5,387,720. These catalysts are more active and deactivate less quickly, which allows longer cycles and a smaller reactor volume.

One subject of the present invention is thus a process for manufacturing acrolein by gas-phase dehydration of glycerol in the presence of strongly acidic solid catalysts with a Hammett acidity of between −9 and −18 and preferably between −10 and −16.

As indicated in U.S. Pat. No. 5,387,720, which refers to the article by K. Tanabe et al. in "Studies in Surface Science and Catalysis", Vol. 51, 1989, chap. 1 and 2, the Hammett acidity is determined by amine titration using indicators or by adsorption of a base in the gas phase. The catalysts satisfying the acidity criterion $H_0$ of between −9 and −18 may be chosen from natural or synthetic siliceous materials or acidic zeolites; mineral supports, such as oxides, coated with mono-, di-, tri- or polyacidic inorganic acids; oxides or mixed oxides, or alternatively heteropolyacids.

The catalysts are advantageously chosen from zeolites, Nafion® composites (based on sulfonic acid of fluorinated polymers), chlorinated aluminas, phosphotungstic and/or silicotungstic acids and acid salts, and various solids of metal oxide type such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silico-aluminate $SiO_2$—$Al_2O_3$, impregnated with acidic functions such as borate $BO_3$, sulfate $SO_4$, tungstate $WO_3$, phosphate $PO_4$, silicate $SiO_2$ or molybdate $MoO_3$.

The preferred catalysts are sulfate zirconias, phosphate zirconias, tungsten zirconias, siliceous zirconias, sulfate titanium or tin oxides, and phosphate aluminas or silicas.

The reaction may be performed in the presence of molecular oxygen. The molecular oxygen may be present in the form of air or in the form of a mixture of gases containing molecular oxygen. The amount of oxygen is chosen so as to be outside the flammability range at any point in the plant. From FIG. 4 of US patent application 2004/15012, the maximum oxygen content, in an acrolein/$O_2$/$N_2$ mixture is about 7% by volume in order to be entirely outside the flammability range. The molecular oxygen content will generally be chosen so as not to exceed 7% relative to the mixture of gases entering the reaction (mixture of glycerol/$H_2O$/oxygen/inert gases). Preferably, the oxygen content is less than 7% relative to the dry gas mixture leaving the reactor (mixture of acrolein/oxygen/inert gases).

The reaction according to the invention is performed in the gas phase. Various process technologies may be used and are known to those skilled in the art, i.e. a fixed-bed process, a fluidized-bed process or a circulating fluidized-bed process.

The selection of the optimum process is made as a function of various criteria; the fixed-bed process has the advantage of simplicity; the fluidized-bed processes make it possible to continuously discharge the spent catalyst and to permanently recharge fresh catalyst without stopping the production, with the possibility of being isothermic. The circulating fluidized-bed process has the advantage of optimizing the reaction selectivity by permanently returning freshly regenerated catalyst into the reactor, while at the same time compensating for the energy exchange between the reactor and the regenerator. The regeneration of the catalyst may be performed with oxygen, hydrogen or with other treatments such as washing with solvents and/or treatment with $H_2O_2$.

According to one particular embodiment of the invention, the process is performed in a reactor of the plate heat exchanger type. This reactor consists of plates forming between themselves circulation channels that can contain a catalyst. This technology has many advantages in terms of heat exchange, associated with high heat exchange capacity. Thus, this type of reactor is particularly suitable for removing heat easily in the case of exothermic reactions, or for supplying heat in the start-up phases of reactions or in the case of endothermic reactions. More particularly, this reactor makes it possible either to heat or to cool the catalyst. The heat exchange is particularly efficient with the circulation of a heat-exchange fluid in the system. The plates may be assembled in modules, which gives greater flexibility, whether as regards the size of the reactor, its maintenance or the replacement of the catalyst. Systems that may be suitable for the process of the invention are, for example, the reactors described in documents EP 995 491 or EP 1 147 807, the content of which is incorporated by reference. These reactors are particularly suitable for the catalytic conversion of reaction media, specifically gaseous reaction media, such as those used in the present invention. The plate heat exchanger used for the preparation of (meth)acrolein or (meth)acrylic acid via catalytic oxidation of C3 or C4 precursors, described in document US 2005/0020851, may also be suitable for the manufacture of acrolein via dehydration of glycerol, which is the subject of the present invention.

The experimental conditions of the reaction are preferably a temperature of between 250° C. and 350° C. and a pressure of between 1 and 5 bar. It has been observed that a lower temperature leads to a reduction of the glycerol conversion yield, but, at the same time, the selectivity towards acrolein is increased. To avoid consecutive reactions and the formation of unwanted products, it is important to limit the residence time in the reactor; moreover, by increasing the residence time, it is also possible to have higher conversions. It is especially desirable to increase the contact time (residence time) of the reagents in the region of the catalyst in order to compensate for a decrease in the degree of conversion when a lower reaction temperature is used.

Glycerol is available inexpensively in the form of aqueous solutions. Advantageously, an aqueous glycerol solution with a concentration of between 10% and 50% and preferably between 15% and 30% by weight is used in the reactor. The concentration should not be too high, so as to avoid spurious reactions such as the formation of glycerol ethers or reactions between the acrolein produced and the glycerol. Moreover, the glycerol solution should not be too dilute on account of the energy cost involved in the evaporation of the aqueous glycerol solution. In any case, the concentration of the glycerol solution may be adjusted by recycling the water produced by the reaction. In order to reduce the glycerol transportation and storage costs, the reactor may be fed with concentrated solution of 40% to 100% by weight of glycerol, dilution to the optimum content being performed by recycling some of the steam produced by the reaction and of the dilution water. Similarly, the recovery of heat at the reactor outlet may also allow the glycerol solution feeding the reactor to be vaporized.

Glycerol derived from the methanolysis of plant oils in basic medium may contain certain impurities such as sodium chloride or sulfate, non-glycerol organic matter, and methanol. The presence of sodium salts is in particular detrimental to the catalytic dehydration reaction since these salts are capable of poisoning the acidic sites. A pretreatment of the glycerol by ion exchange may be envisaged.

Compared with the conventional process for preparing acrolein by selective oxidation of propylene, the acrolein produced according to the process of the invention may contain impurities of different nature or in different amount. According to the envisaged use, synthesis of acrylic acid, synthesis of methionine or fine chemistry reactions, it may be envisaged to purify the acrolein according to the techniques known to those skilled in the art. More particularly, the by-products may be recovered and incinerated, thus producing vapour or energy. The energetic upgrading of the by-products of the glycerol dehydration reaction furthermore makes it possible to greatly reduce the greenhouse-gas emissions of the process, compared with the conventional process, for which the $CO_2$ produced is derived from fossil carbon during the incineration of the by-products.

The examples that follow illustrate the present invention without, however, limiting its scope.

EXAMPLES

In the examples, a tubular reactor consisting of a tube 85 cm long and with an inside diameter of 6 mm is used to perform the glycerol dehydration reaction in the gas phase at atmospheric pressure. This reactor is placed in a heated chamber maintained at the reaction temperature, which is 300° C., unless otherwise indicated. The catalysts used are ground and/or pelletized to obtain particles of 0.5 to 1.0 mm. 10 ml of catalyst are loaded into the reactor to form a catalytic bed 35 cm long. This bed is maintained at the reaction temperature for 5 to 10 minutes before introducing the reagents. The reactor is fed with an aqueous solution containing 20% by weight of glycerol at a mean feed flow rate of 12 ml/h. The aqueous glycerol solution is vaporized in the heated chamber, and then passes over the catalyst. The calculated contact time is about 2.9 sec. The duration of a catalyst test is about 7 hours, which corresponds to about 80 ml of aqueous glycerol solution passed over the catalyst. After reaction, the products are condensed in a trap refrigerated with crushed ice.

Samples of the effluents are collected periodically. For each sample collection, the flow is interrupted and a gentle flow of nitrogen is passed through the reactor to purge it. The trap at the reactor outlet is then replaced, the nitrogen flow is stopped and the reactor is returned under a flow of reagent. The test is continued until appreciable deactivation of the catalyst is noted.

For each experiment, the total mass of products entering and leaving is measured, which allows a mass balance to be determined. Similarly, the products formed are analysed by chromatography. Two types of analysis are performed:

an analysis by chromatography on a filled column (FFAP column 2 m*⅛") on a Carlo Erba chromatograph equipped with a TCD detector. The quantitative analysis is performed with an external standard (2-butanone);

an analysis by chromatography on a capillary column (FFAP column 50 m*0.25 mm) on an HP6890 chromatograph equipped with an FID detector with the same samples stored at −15° C.

The first method is particularly suitable for rapid analysis of the products, and especially the yield of acrolein. The second method is used to have a more precise analysis of all the reaction by-products. Moreover, analyses by GMS or by chromatography after silylation were performed to confirm these results.

The products thus quantified are the unreacted glycerol, the acrolein formed and the by-products such as hydroxypropanone, acetaldehyde, propanaldehyde, acetone and phenol.

In the examples that follow, the glycerol conversion, the acrolein selectivity and the yields of the various products are defined as follows:

glycerol conversion (%)=100−number of moles of glycerol remaining/number of moles of glycerol introduced;

acrolein yield (%)=number of moles of acrolein produced/number of moles of glycerol introduced;

acrolein selectivity (%)=100*number of moles of acrolein produced/number of moles of glycerol reacted.

The acetone or hydroxypropanone yield is calculated as for the acrolein yield:

acetaldehyde yield (%)=⅔*number of moles of acetaldehyde produced/number of moles of glycerol introduced.

phenol yield (%)=2*number of moles of phenol produced/number of moles of glycerol introduced.

All the results are expressed as molar percentages relative to the glycerol introduced.

Examples 1 and 1a (Comparative of the Prior Art)

10 ml of $H_3PO_4$/alpha-alumina catalyst with a Hammett acidity $H_0$ of between −3 and −5.6, prepared as described in U.S. Pat. No. 5,387,720, representing a mass of 10 g, were loaded into the reactor. The catalyst was prepared in the following manner: 15.9 g of alpha-alumina from Ceramtec (Ref EO-19—specific surface area 0.7 $m^2/g$—mean pore diameter 2.5 μm—apparent porosity 65%—supplied in the form of rings and ground so as to retain only the particles of diameter 1-1.4 mm) were impregnated with 4 g of a 20% by weight phosphoric acid solution (prepared by addition of 16.25 ml of water and 5 g of 85% by weight phosphoric acid). The solid is then dried on a rotavapor at 80° C. and used directly for Example 1. For Example 1a, the solid underwent an additional activation in air at 300° C. for 3 hours in order to fix the phosphoric acid to the support. The results are collated in Table 1 below:

TABLE 1

| | Example 1 | | | | Example 1a | | | |
|---|---|---|---|---|---|---|---|---|
| | Cumulative glycerol introduced (g) | | | | | | | |
| | 8 | 16 | 25 | 32 | 8 | 16 | 24 | 32 |
| Glycerol conversion | 91 | 69 | 42 | 17 | 70 | 37 | 9 | 8 |
| Acrolein yield | 54.5 | 32.2 | 20.6 | 3.8 | 42.1 | 18.2 | 4.6 | 3.1 |
| Acrolein selectivity | 60 | 46 | 49 | 23 | 60 | 50 | 50 | 41 |
| Hydroxypropanone yield | 12.3 | 9.3 | 6.5 | 2.1 | 10.3 | 4.8 | 0.0 | 0.0 |
| Acetaldehyde yield | 0.1 | 0.0 | 0.0 | 0.0 | 0.0 | 0.0 | 0.0 | 0.0 |
| Propanaldehyde yield | 0.3 | 0.2 | 0.1 | 0.0 | 0.0 | 0.0 | 0.0 | 0.0 |
| Acetone yield | 0.0 | 0.0 | 0.0 | 0.0 | 0.0 | 0.0 | 0.0 | 0.1 |
| Phenol yield | 1.0 | 0.1 | 0.1 | 0.0 | 0.8 | 0.0 | 0.0 | 0.0 |
| Material balance (mass collected/mass introduced) | 98.6 | 98.7 | nd | 98.9 | 98.5 | 98.9 | 98.0 | 99.0 |
| Quantified product balance (products assayed/glycerol introduced) | 77.6 | 72.6 | 84.9 | 89.4 | 83.2 | 86.2 | 95.5 | 95.6 |

Rapid deactivation of the catalyst is observed.

Example 2

A sulfate zirconia (90% $ZrO_2$-10% $SO_4$) from Daiichi Kigenso (supplier reference H1416) is used as catalyst. This catalyst has a loss on ignition at 1000° C. of 8.81% and a specific surface area of 54.3 $m^2$/g (BET, 1 point). The acidity $H_0$ is equal to −16 according to the table on page 71 of the publication on acid-base catalysis (C. Marcilly) Vol. 1, published by Technip (ISBN No. 2-7108-0841-2). 10 ml of catalyst, representing a mass of 16.5 g, were loaded into the reactor.

The results are given in Table 2 below.

TABLE 2

| | Cumulative glycerol introduced (g) | | | | | |
|---|---|---|---|---|---|---|
| | 9 | 17 | 27 | 36 | 44 | 53 |
| Glycerol conversion | 100 | 99 | 96 | 91 | 89 | 84 |
| Acrolein yield | 34.0 | 43.3 | 40.6 | 36.0 | 33.8 | 35.4 |
| Acrolein selectivity | 34 | 44 | 42 | 39 | 38 | 42 |
| Hydroxypropanone yield | 8.5 | 13.8 | 13.7 | 14.6 | 15.1 | 14.3 |
| Acetaldehyde yield | 5.6 | 4.2 | 3.4 | 2.9 | 2.9 | 3.4 |
| Propanaldehyde yield | 12.4 | 9.7 | 7.2 | 6.5 | 6.7 | 7.8 |
| Acetone yield | 0.0 | 0.0 | 0.3 | 0.0 | 0.0 | 0.0 |

TABLE 2-continued

| | Cumulative glycerol introduced (g) | | | | | |
|---|---|---|---|---|---|---|
| | 9 | 17 | 27 | 36 | 44 | 53 |
| Phenol yield | 1.9 | 0.4 | 0.4 | 0.3 | 0.3 | 0.3 |
| Material balance (mass collected/mass introduced) | 96.5 | 99.0 | 98.4 | 99.3 | 98.6 | 99.5 |
| Quantified product balance (products assayed/glycerol introduced) | 62.5 | 72.8 | 70.0 | 69.0 | 69.6 | 77.2 |

This type of catalyst deactivates less quickly than that of Example 1.

Examples 3 and 3a 10 ml of 40% Nafion/$SiO_2$ composite prepared according to the procedure described in the publication by Hölderich and Harmer, Green Chemistry 2000, 2, pp. 7-14, representing a mass of 4.77 g, were loaded into the reactor. This type of catalyst has an acidity $H_0$ of about −12 according to a commercial notice.

The results are given in Table 3 below.

TABLE 3

| | Cumulative glycerol introduced (g) | | | | | | | |
|---|---|---|---|---|---|---|---|---|
| | 8 | 16 | 24 | 33 | 41 | 50 | 58 | 67 |
| Glycerol conversion | 100 | 100 | 100 | 97 | 92 | 87 | 80 | 73 |
| Acrolein yield | 63.6 | 76.0 | 72.5 | 68.3 | 64.0 | 58.6 | 52.6 | 47.2 |
| Acrolein selectivity | 64 | 76 | 73 | 70 | 69 | 68 | 66 | 65 |
| Hydroxypropanone yield | 5.0 | 9.5 | 9.3 | 9.4 | 9.0 | 8.0 | 7.0 | 6.4 |
| Acetaldehyde yield | 1.3 | 0.5 | 0.4 | 0.3 | 0.2 | 0.2 | 0.2 | 0.1 |
| Propanaldehyde yield | 5.1 | 2.1 | 1.4 | 1.1 | 0.9 | 0.7 | 0.6 | 0.5 |

TABLE 3-continued

| | Cumulative glycerol introduced (g) | | | | | | | |
|---|---|---|---|---|---|---|---|---|
| | 8 | 16 | 24 | 33 | 41 | 50 | 58 | 67 |
| Acetone yield | 0.0 | 0.0 | 0.0 | 0.1 | 0.0 | 0.0 | 0.0 | 0.0 |
| Phenol yield | 2.5 | 1.5 | 1.6 | 0.0 | 1.2 | 1.1 | 1.0 | 0.9 |
| Material balance (mass collected/mass introduced) | 97.5 | 98.8 | 98.8 | 99.5 | 99.0 | 99.5 | 99.0 | 99.0 |
| Quantified product balance (products assayed/glycerol introduced) | 77.5 | 89.7 | 85.5 | 81.7 | 83.3 | 82.1 | 81.6 | 82.0 |

This same catalyst was tested, this time with a reaction temperature of 280° C. instead of 300° C. The results are given in Table 3a below.

TABLE 3a

| | Cumulative glycerol introduced (g) | | | | | | | |
|---|---|---|---|---|---|---|---|---|
| | 8 | 16 | 24 | 32 | 40 | 56 | 72 | 80 |
| Glycerol conversion | 100 | 100 | 100 | 100 | 97 | 93 | 85 | 80 |
| Acrolein yield | 62.3 | 73.2 | 72.5 | 70.8 | 67.3 | 62.1 | 55.0 | 50.4 |
| Acrolein selectivity | 62 | 73 | 72 | 71 | 69 | 67 | 65 | 63 |
| Hydroxypropanone yield | 4.4 | 8.8 | 9.5 | 9.5 | 9.5 | 9.2 | 9.1 | 8.3 |
| Acetaldehyde yield | 1.0 | 0.4 | 0.3 | 0.3 | 0.2 | 0.2 | 0.1 | 0.1 |
| Propanaldehyde yield | 4.9 | 2.2 | 1.7 | 1.4 | 1.0 | 0.9 | 0.6 | 0.6 |
| Acetone yield | 0.0 | 0.0 | 0.0 | 0.0 | 0.0 | 0.0 | 0.0 | 0.0 |
| Phenol yield | 2.5 | 1.7 | 1.4 | 1.2 | 1.0 | 1.0 | 1.0 | 0.9 |
| Material balance (mass collected/mass introduced) | 97.2 | 98.5 | 98.7 | 98.6 | 99.0 | 98.5 | 98.5 | 99.2 |
| Quantified product balance (products assayed/glycerol introduced) | 75.2 | 86.4 | 85.4 | 83.1 | 81.6 | 80.3 | 80.8 | 80.0 |

This type of catalyst is active and selective and deactivates less quickly than that of Example 1.

Example 4

A phosphate zirconia (91.5% $ZrO_2$-8.5% $PO_4$) from Daii-chi Kigenso (Ref. H1418) is used. This catalyst has a loss on ignition at 1000° C. of 4.23% and a specific surface area of 128.7 m²/g. 10 ml of this catalyst, representing a mass of 12.7 g, were loaded into the reactor.

The results are given in Table 4 below.

TABLE 4

| | Cumulative glycerol introduced (g) | | | | | | | |
|---|---|---|---|---|---|---|---|---|
| | 8 | 16 | 24 | 32 | 41 | 49 | 57 | 65 |
| Glycerol conversion | 100 | 100 | 100 | 100 | 99 | 97 | 96 | 95 |
| Acrolein yield | 16.6 | 40.4 | 46.7 | 45.2 | 46.2 | 46.5 | 45.3 | 46.9 |
| Acrolein selectivity | 17 | 40 | 47 | 45 | 46 | 48 | 47 | 49 |
| Hydroxypropanone yield | 0.0 | 9.4 | 13.0 | 13.5 | 14.7 | 15.0 | 15.2 | 16.7 |
| Acetaldehyde yield | 6.9 | 6.3 | 5.0 | 4.7 | 4.3 | 4.0 | 3.5 | 3.7 |

TABLE 4-continued

|  | Cumulative glycerol introduced (g) | | | | | | | |
|---|---|---|---|---|---|---|---|---|
|  | 8 | 16 | 24 | 32 | 41 | 49 | 57 | 65 |
| Propanaldehyde yield | 15.0 | 14.2 | 11.7 | 11.1 | 9.8 | 9.0 | 8.0 | 8.2 |
| Acetone yield | 0.0 | 0.0 | 0.0 | 0.0 | 0.0 | 0.0 | 0.0 | 0.0 |
| Phenol yield | 4.2 | 4.4 | 2.9 | 2.5 | 1.8 | 2.2 | 1.7 | 1.8 |
| Material balance (mass collected/mass introduced) | 95.0 | 98.2 | 95.2 | 97.7 | 97.6 | 98.4 | 97.9 | 97.9 |
| Quantified product balance (products assayed/glycerol introduced) | 42.7 | 74.6 | 79.3 | 77.0 | 77.4 | 79.4 | 77.3 | 82.3 |

Example 5

A tungsten zirconia (90.7% $ZrO_2$-9.3% $WO_3$) from Daiichi Kigenso (supplier reference H1417) is used. This catalyst has a loss on ignition at 1000° C. of 1.75% and a specific surface area of 47.4 $m^2/g$ (BET, 1 point). The acidity $H_0$ is equal to −14.5 according to the table on page 71 of the publication on acid-base catalysis (C. Marcilly) Vol. 1, published by Technip (ISBN No. 2-7108-0841-2).

10 ml of catalyst, representing a mass of 17 g, were loaded into the reactor.

The results are given in Table 5 below.

TABLE 5

|  | Cumulative glycerol introduced (g) | | | | | | | |
|---|---|---|---|---|---|---|---|---|
|  | 8 | 16 | 25 | 32 | 39 | 48 | 61 | 78 |
| Glycerol conversion | 100 | 100 | 100 | 100 | 100 | 100 | 100 | 100 |
| Acrolein yield | 46.9 | 69.2 | 71.6 | 72.1 | 71.4 | 72.7 | 73.5 | 73.1 |
| Acrolein selectivity | 47 | 69 | 72 | 72 | 71 | 73 | 74 | 73 |
| Hydroxypropanone yield | 0.3 | 4.5 | 7.4 | 8.6 | 6.7 | 9.7 | 10.8 | 12.9 |
| Acetaldehyde yield | 4.7 | 4.4 | 4.0 | 3.8 | 3.7 | 3.4 | 2.7 | 1.7 |
| Propanaldehyde yield | 8.7 | 7.4 | 7.0 | 6.7 | 6.6 | 5.4 | 5.6 | 3.6 |
| Acetone yield | 2.3 | 3.0 | 2.5 | 2.4 | 2.4 | 2.3 | 1.7 | 1.1 |
| Phenol yield | 2.1 | 1.5 | 1.3 | 1.2 | 0.1 | 1.0 | 0.2 | 0.0 |
| Material balance (mass collected/mass introduced) | 96.8 | 98.2 | 98.4 | 99.0 | 97.0 | 99.0 | 99.0 | 98.6 |
| Quantified product balance (products assayed/glycerol introduced) | 65.0 | 89.9 | 93.9 | 94.7 | 90.9 | 94.5 | 94.6 | 92.3 |

This catalyst maintains a high yield largely superior to the performance of the catalyst of Example 1.

Example 6

10 ml of sulfate zirconia from Daiichi Kigenso, as described in Example 2 (H1416), representing a mass of 16.5 g, were loaded into the reactor. The reaction is performed this time in the presence of molecular oxygen, at a flow rate of 0.8 l/h. The results are given in Table 6 below.

TABLE 6

|  | Cumulative glycerol introduced (g) | | |
|---|---|---|---|
|  | 9 | 18 | 27 |
| Glycerol conversion | 100 | 100 | 100 |
| Acrolein yield | 42.3 | 53.8 | 52.5 |
| Acrolein selectivity | 42 | 54 | 52 |
| Hydroxypropanone yield | 0.0 | 0.0 | 0.0 |
| Acetaldehyde yield | 10.3 | 9.1 | 8.2 |

TABLE 6-continued

|  | Cumulative glycerol introduced (g) | | |
|---|---|---|---|
|  | 9 | 18 | 27 |
| Propanaldehyde yield | 4.9 | 3.7 | 4.0 |
| Acetone yield | 0.0 | 0.4 | 0.0 |
| Phenol yield | 0.0 | 0.0 | 0.3 |
| Material balance (mass collected/mass introduced) | 96.5 | 98.0 | 98.0 |

TABLE 6-continued

|  | Cumulative glycerol introduced (g) | | |
| --- | --- | --- | --- |
|  | 9 | 18 | 27 |
| Quantified product balance (products assayed/glycerol introduced) | 57.5 | 66.9 | 65.0 |

The addition of molecular oxygen makes it possible to achieve higher yields by limiting the formation of by-products.

The invention claimed is:

1. Process for manufacturing acrolein by gas-phase dehydration of glycerol in the presence of a strongly acidic solid catalyst with a Hammett acidity $H_0$ of between −9 and −18.

2. Process according to claim 1, characterized in that the catalyst has a Hammett acidity $H_0$ of between −10 and −16.

3. Process according to claim 1, characterized in that the catalyst is selected from natural siliceous materials, synthetic siliceous materials, acidic zeolites, mono-, di-, tri- or polyacidic inorganic acids, oxides, mixed oxides, or heteropolyacids.

4. Process according to claim 1, characterized in that the catalyst is chosen from zeolites, composites based on sulfonic acid of fluorinated polymers, chlorinated aluminas, phosphotungstic acids and salts, silicotungstic acids and acid salts, and solids of metal oxide.

5. Process according to claim 1, characterized in that the catalyst is selected from sulfate zirconias, phosphate zirconias, tungsten zirconias, siliceous zirconias, sulfate titanium oxides, sulfate tin oxides, phosphate aluminas or phosphate silicas.

6. Process according to claim 1, characterized in that the glycerol is in the form of an aqueous solution with a concentration of between 10% and 50% by weight.

7. Process according to claim 1, characterized in that the gas-phase dehydration is performed in the presence of molecular oxygen, in an amount chosen so as to be outside the flammability range at any point in the process.

8. Process according to claim 7, characterized in that the molecular oxygen is in the form of air or in the form of a mixture of gases containing molecular oxygen.

9. Process according to claim 1, characterized in that the gas-phase dehydration is performed in a fixed-bed reactor, a fluidized-bed reactor, a circulating fluidized-bed reactor or in a plate heat exchanger.

10. Process according to claim 3, characterized in that said di-, tri- or polyacidic inorganic acids is supported on a mineral supports selected from oxides.

11. Process according to claim 4, characterized in that the solids of metal oxide are selected from tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silico-aluminate $SiO_2$-$Al_2O_3$.

12. Process according to claim 1, characterized in that the glycerol is in the form of an aqueous solution with a concentration of between 15% and 30% by weight in the reactor.

* * * * *